(12) United States Patent
Uematsu

(10) Patent No.: US 8,692,050 B2
(45) Date of Patent: Apr. 8, 2014

(54) MEDICATED PATCH

(75) Inventor: Masanori Uematsu, Ayauta-gun (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 436 days.

(21) Appl. No.: 12/279,947

(22) PCT Filed: Apr. 25, 2006

(86) PCT No.: PCT/JP2006/308631
§ 371 (c)(1),
(2), (4) Date: Aug. 19, 2008

(87) PCT Pub. No.: WO2007/097047
PCT Pub. Date: Aug. 30, 2007

(65) Prior Publication Data
US 2009/0221947 A1 Sep. 3, 2009

(30) Foreign Application Priority Data

Feb. 20, 2006 (JP) .................................. 2006-042496

(51) Int. Cl.
*A61F 13/00* (2006.01)
(52) U.S. Cl.
USPC .................. 602/48; 602/42; 602/52; 602/54; 602/57; 602/58
(58) Field of Classification Search
USPC .............................. 602/42, 48, 52, 54, 57–58; 424/443–447
See application file for complete search history.

(56) References Cited

U.S. PATENT DOCUMENTS

| 4,390,519 A | * | 6/1983 | Sawyer | 424/447 |
| 4,664,106 A | * | 5/1987 | Snedeker | 602/57 |
| 4,913,138 A | * | 4/1990 | Yoshida et al. | 602/57 |
| 4,915,765 A | * | 4/1990 | Metters | 156/267 |

(Continued)

FOREIGN PATENT DOCUMENTS

| JP | 1-65025 U | 4/1989 |
| JP | 8-112305 A | 5/1996 |

(Continued)

OTHER PUBLICATIONS

Abstract of Japanese Patent Document No. 2001-505211T dated Apr. 17, 2001 w/English translation of claims and corresponding US patent document cited as A1 above.

(Continued)

*Primary Examiner* — Tatyana Zalukaeva
*Assistant Examiner* — Camtu Nguyen
(74) *Attorney, Agent, or Firm* — Crowell & Moring LLP

(57) ABSTRACT

A medicated patch is provided which is covered with a liner that enables one to remove the liner unconsciously and readily without losing the initial stickiness of the medicated patch. The external medicated patch includes a backing, an aqueous adhesive drug-containing matrix that is spread substantially entirely over one surface of the backing, and a liner that is larger in size than the surface of the drug-containing matrix to which the liner is attached. The liner larger in size than the surface of the drug-containing matrix to which the liner is attached includes an unattached area that extends from the surface of the drug-containing matrix, or an unattached slack portion that projects upward from the surface of the drug-containing matrix at a position on the surface of the drug-containing matrix.

1 Claim, 5 Drawing Sheets

(56) References Cited

U.S. PATENT DOCUMENTS

| | | | |
|---|---|---|---|
| 5,409,703 A * | 4/1995 | McAnalley et al. | 424/435 |
| 5,779,632 A * | 7/1998 | Dietz et al. | 600/391 |
| 6,277,458 B1 | 8/2001 | Dirksing et al. | |
| 6,440,513 B1 | 8/2002 | Kibele et al. | |
| 6,465,709 B1 * | 10/2002 | Sun et al. | 602/48 |
| 6,582,403 B1 * | 6/2003 | Bierman et al. | 604/174 |
| 7,585,554 B2 * | 9/2009 | Johnson et al. | 428/40.1 |

FOREIGN PATENT DOCUMENTS

| | | |
|---|---|---|
| JP | 2000-175960 A | 6/2000 |
| JP | 2000-175961 A | 6/2000 |
| JP | 2000-219622 A | 8/2000 |
| JP | 2000-351717 A | 12/2000 |
| JP | 2000-351727 A | 12/2000 |
| JP | 2001-505211 A | 4/2001 |
| JP | 2002-539502 A | 11/2002 |
| JP | 2003-70898 A | 3/2003 |
| JP | 2003-135514 A | 5/2003 |

OTHER PUBLICATIONS

Abstract of Japanese Patent Document No. 2002-539502T dated Nov. 19, 2002 with corresponding US patent document cited as A2 above.

International Search Report dated Jul. 18, 2006 (two (2) pages).

Mechanical Translation of JP 2000-175961 A (B4 previously filed on Aug. 14, 2008).

Mechanical Translation of JP 2003-135514 A (B5 previously filed on Aug. 14, 2008).

Mechanical Translation of JP 2003-070898 A (B7 previously filed on Aug. 14, 2008).

Mechanical Translation of JP 08-112305 A (B8 previously filed on Aug. 14, 2008).

Mechanical Translation of JP 2000-219622 A (B1 previously filed on Aug. 14, 2008).

Mechanical Translation of JP 2000-175960 A (B3 previously filed on Aug. 14, 2008).

* cited by examiner

Fig. 1.1
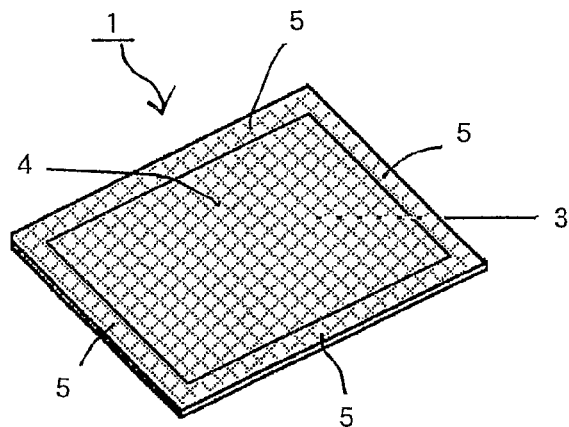
Fig. 1.2
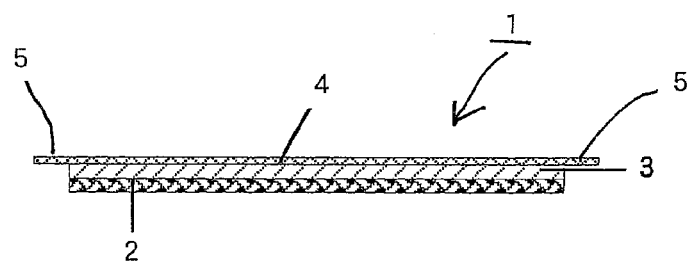
Fig. 1.3
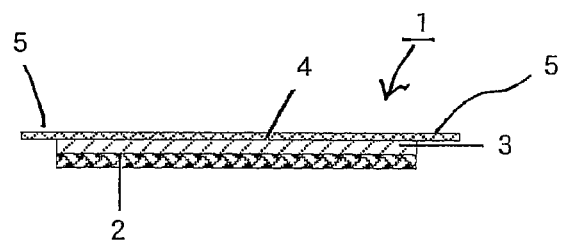

Fig. 2.1
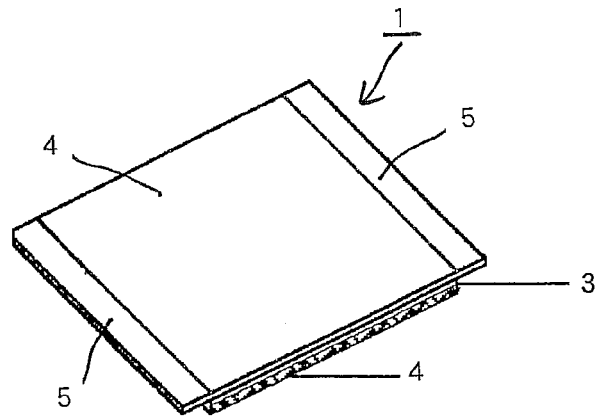
Fig. 2.2
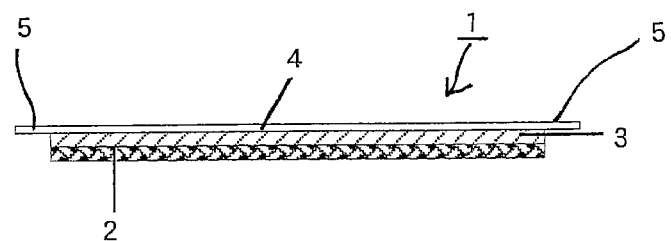
Fig. 2.3
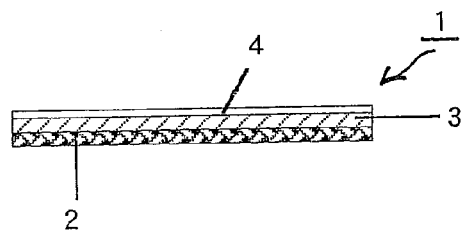

Fig. 3.1
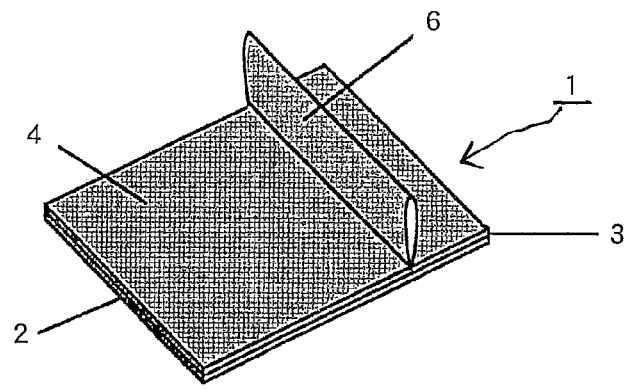
Fig. 3.2
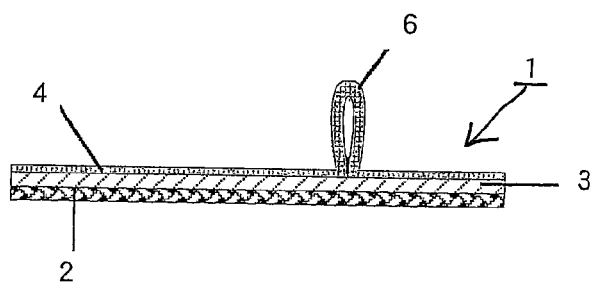
Fig. 4.1
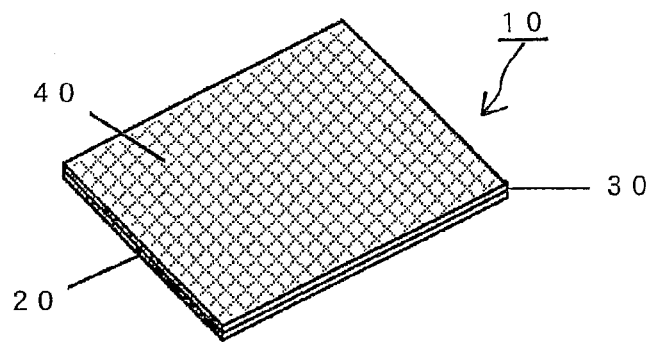

Fig. 4.2
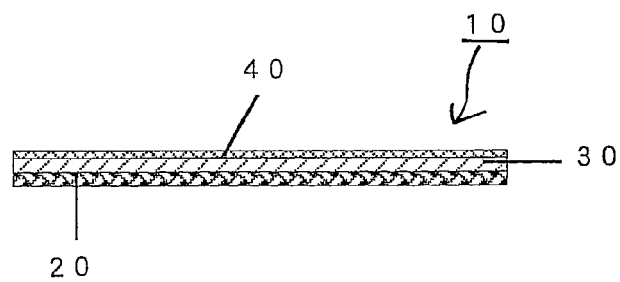
Fig. 5.1
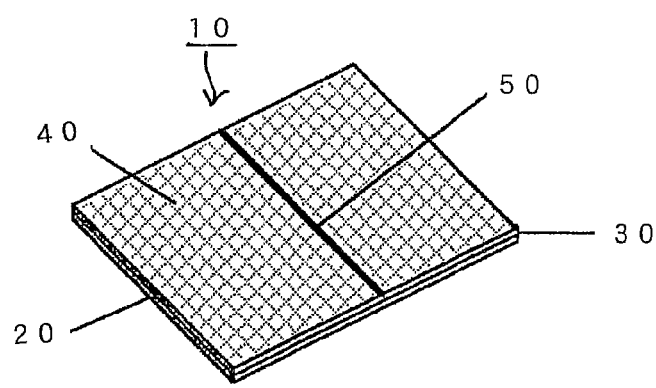
Fig. 5.2
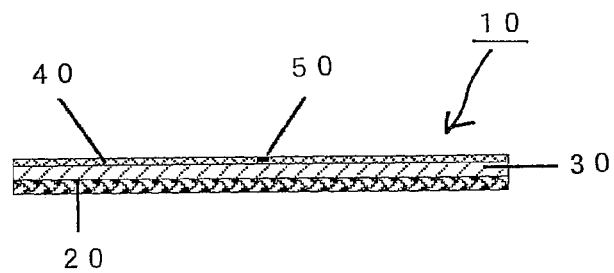

MEDICATED PATCH

TECHNICAL FIELD

The present invention relates to aqueous external medicated patches intended for the treatment of inflammation, pain and other symptoms, as well as for cooling. More particularly, the present invention relates to external medicated patches that include a peelable film (i.e., liner) that can be peeled easily and quickly not only by non-disabled people, but also by aged and other people with a disability.

BACKGROUND ART

Medicated patches that have antiinflammatory, analgesic or cooling effects are now widely used in the symptomatic treatment of lumbago, joint pain, shoulder stiffness and other symptoms caused by aging, hard work and other conditions.

Conventional medicated patches, including poultice-type patches, typically have a multilayer structure. As an example, a conventional medicated patch 10 is shown in FIG. 4. The medicated patch 10 has a multilayer structure including a white or skin-colored backing 20, an adhesive drug-containing matrix 30 that is spread substantially entirely over one surface of the backing, and a sheet of liner 40 that entirely covers the drug-containing matrix.

Certain medicated patches, such as medicated patch 10 shown in FIG. 5, include a tear line 50 at the middle of the liner 40. To apply this type of medicated patch, the user stretches the patch to tear the liner at the tear line and holds the exposed drug-containing matrix 30 against the application site for temporal tacking while peeling off the torn pieces of the liner, so as to finally apply the patch to the application site (See, for example, Patent Document 1).

These medicated patches have the following drawbacks regarding the removal of the liner upon application.

The common medicated patch 10 as shown in FIG. 4 requires the user to peel the liner 40 by rubbing the edge of the medicated patch 10 with fingers, thus causing the liner 40 to partially come off. Many of the patients are aged people who have decreased dexterity and this rubbing and pealing is difficult and complicated for many of the aged people.

The medicated patch shown in FIG. 5 has been developed to facilitate the above-described process. However, tearing the liner 40 by forcibly stretching the medicated patch 10 from both right and left sides causes the patch to wrinkle. As a result, even if the user manages to peel the liner from both sides and apply the medicated patch to the application site, it is often necessary to remove the patch from the application site and reapply it after removing wrinkles. The reapplied patch often loses its initial stickiness and tends to come off during daily activities.

Furthermore, aged people are used to the conventional peeling method shown in FIG. 6 and therefore tend to peel the liner 40 by rubbing the edge of the medicated patch 10. In many cases, this will lead to the liner being torn along the tear line 50, forcing the user to repeat the process of rubbing the edge of the remaining film to peel it. Even if the liner contains a clearly visible instruction on how to peel the film, such instructions are neglected by most of the patients.

Some medicated patches have been proposed to address these problems. In one such medicated patch, the liner attached to the drug-containing matrix consists of two separate films. The edge of one film is folded upward along the mid-portion of the drug-containing matrix and the other film is overlaid on top of the fold of the first film. This construction assists the user in peeling the liner (See, for example, Patent Documents 2 and 3).

In another medicated patch, one side of the backing is not coated with the drug-containing matrix. In still another medicated patch, one corner of the backing and the drug-containing matrix is cut so that part of the protective sheet is exposed (See, for example, Patent Documents 4 and 5).

However, the medicated patch in which the drug-containing matrix is covered with two separate liners requires complex procedures to produce. In addition, the upward folding of the edge of one of the liners that is arranged below the other film cannot be effected uniformly.

The medicated patch in which one side of the backing is not coated with the drug-containing matrix tends to come off from the uncoated side during the application. The medicated patch in which one corner of the backing and the drug-containing matrix is cut to expose part of the protective sheet still presents difficulty to aged people trying to pinch the exposed part of the protective sheet since the exposed part is not large enough.

Patent Document 1: Japanese Laid-Open Patent Publication Hei 8-112305
Patent Document 2: Japanese Laid-Open Patent Publication 2000-219622
Patent Document 3: Japanese Laid-Open Patent Publication 2000-351717
Patent Document 4: Japanese Laid-Open Patent Publication 2000-175960
Patent Document 5: Japanese Laid-Open Patent Publication 2000-175961

DISCLOSURE OF THE INVENTION

Problems to be Solved by the Invention

Accordingly, it is an object of the present invention to provide a medicated patch using a liner that enables the patient, even one who is accustomed to the conventional peeling method of the liner used in the conventional medicated patches, to remove the liner unconsciously and readily without losing the initial stickiness of the medicated patch.

Means for Solving the Problems

To achieve the above-described object, the external medicated patch of claim 1, which forms an essential aspect of the present invention, includes a backing, an aqueous adhesive drug-containing matrix that is spread substantially entirely over one surface of the backing, and a liner that is larger in size than the surface of the drug-containing matrix to which the liner is attached.

The external medicated patch of claim 2, which forms a more specific aspect of the present invention, is the medicated patch according to claim 1 in which the liner larger in size than the surface of the drug-containing matrix to which the liner is attached includes an unattached area that extends from each side of the surface of the drug-containing matrix. The external medicated patch of claim 3 is the medicated patch according to claim 1 in which the liner larger in size than the surface of the drug-containing matrix to which the liner is attached includes an unattached area that extends from any one or two sides of the surface of the drug-containing matrix.

The external medicated patch of claim 4, which forms another specific aspect of the present invention, is the medicated patch according to claim 1 in which the liner larger in size than the surface of the drug-containing matrix to which the liner is attached includes an unattached slack portion that projects upward from the surface of the drug-containing matrix at a position on the surface of the drug-containing matrix.

The external medicated patch of claim 5 is the external medicated patch according to claim 2 or 3 in which the liner larger in size than the surface of the drug-containing matrix to which the liner is attached includes an unattached slack portion that projects upward from the surface of the drug-containing matrix at a position on the surface of the drug-containing matrix.

In the external medicated patch of claim 4 or 5 provided in accordance with the present invention, the unattached slack portion that projects upward is provided so as to extend from sides in the longitudinal direction of the external medicated patch along the width of the surface of the drug-containing matrix.

In the external medicated patch provided in accordance with the present invention, the liner attached to the surface of the drug-containing matrix is larger in size than the surface of the drug-containing matrix so that it includes an area unattached to the surface of the drug-containing matrix. This construction facilitates the removal of the liner.

Effect of the Invention

In the above-proposed external medicated patch of the present invention, the step resulting from the difference in area between the liner and the drug-containing matrix, i.e., the area of the liner unattached to the surface of the drug-containing matrix, provides a starting point for the peeling of the liner from the surface of the drug-containing matrix. This construction allows the user to readily peel the liner without rubbing the edge of the medicated patch with fingers.

Thus, the liner does not require particular dexterity for its removal and can therefore be readily and unconsciously peeled by aged or other people with a disability.

Should a user fail to peel the liner in a proper manner, the user can still peel it without any difficulty using the conventional method in which the user rubs the edge of the backing of the medicated patch with the fingers.

Since the medicated patch of the present invention enables unconscious peeling of the liner, it eliminates the need to include instructions on how to peel the liner on the film. As a result, the associated cost can be reduced, making the medicated patch cost-effective.

In addition, since the liner used in the medicated patch of the present invention is a single sheet of film, it takes significantly less time to peel the liner of the present invention than it takes to peel the liner consisting of two separate films as shown in FIG. 5. The liner of the present invention also has a reduced frequency of failed application.

BEST MODE FOR CARRYING OUT THE INVENTION

The present invention essentially concerns an external medicated patch that includes a backing, an aqueous adhesive drug-containing matrix that is spread substantially entirely over one surface of the backing, and a liner that is larger in size than the surface of the drug-containing matrix to which the liner is attached.

The liner for use in the medicated patch of the present invention may be a plastic film formed of plastics, such as cast polypropylene (CPP), oriented polypropylene (OPP), polyethylene terephthalate (PET), polybutylene terephthalate (PBT), polyethylene, polyester, polyurethane, polyvinyl chloride and polystyrene, paper, synthetic paper, synthetic resin or a composite film formed of a laminate thereof; an aluminum foil or aluminum-deposited film laminated with any of the above-described materials; or each or a composite of the above-described materials that is treated with silicone, is embossed, has a printed pattern or is colored.

The liner preferably has a thickness in the range of 6 μm to 200 μm, and preferably in the range of 12 μm to 75 μm. The liner with a thickness of less than 6 μm is not preferred as it tends to wrinkle during the production. The liner with a thickness of greater than 200 μm is not preferred, either, since the thick film is difficult to cut and expensive, leading to an increased cost.

The liner of the present invention is preferably embossed to prevent slipping of the fingers upon removal of the film. The liner is preferably embossed either entirely or partially, for example, in the tab to be held by the fingers.

The liner may or may not be embossed and is preferably embossed with any pattern that provides a good grip for the fingers, such as diamond pattern, lattice pattern, hexagonal pattern, wave pattern and various other patterns.

To clearly indicate to the user the (trade) name of the medicated patch product and necessary instructions, characters, symbols, illustrations and other indicative marks may be provided on the liner. The liner may also be colored.

The backing for use in the external medicated patch of the present invention may be woven fabric, non-woven fabric or a laminate thereof and may or may not be stretchable.

Specific examples of the material for the backing include natural fibers, including bast fibers, such as paper, cotton, hemp and jute, cellulose fibers, such as leaf fibers including, for example, manila hemp, animal fibers, such as wool, and protein fibers, such as silk fibers and feather fibers; regenerated fibers, including regenerated cellulose fibers, such as rayon and cuprammonium rayon, and regenerated protein fibers; semi-synthetic fibers, including cellulose acetate fibers and promix; nylon alamide fibers; polyethylene terephthalate fibers; polyester fibers; acrylic fibers; polyolefin fibers, including polyethylene fibers and polypropylene fibers; polyvinyl alcohol fibers; polyvinyl chloride fibers; polyvinylidene chloride fibers; polyvinyl chloride-based fibers; polyurethane fibers; polyoxymethylene fibers; polytetrafluoroethylene fibers; poly(p-phenylene benz-bisthiazole) fibers; and polyimide fibers. These fibers may be used either individually or in combination to make a woven or non-woven fabric for use in the present invention.

The material for the backing is properly selected based on the tensile strength, thickness and stretchability required for a particular application site, as well as drug transfer to the backing.

The drug-containing matrix for use in the external medicated patch of the present invention contains a base and a drug contained in the base and is suitable for medicated patches used, for example, as external poultice-type patches. The drug-containing matrix also contains moisture to enhance the effect of the active ingredient on the skin. The drug-containing matrix has stickiness and does not soften at room temperature or a higher temperature so that it retains moderate cohesiveness that prevents the drug-containing matrix from remaining on the skin.

A thickener may be used to form the base of the drug-containing matrix. The thickener serves to stably maintain the water content of the drug-containing matrix at about 30% to 80% and preferably shows good water retention. Specific examples of the thickener include water-soluble polymers, including natural polymers, such as plant-based polymers (such as guar gum, locust bean gum, carrageenan, alginic acid, sodium alginate, agar, gum arabic, tragacanth gum, karaya gum, pectin and starch), microorganism-based polymers (such as xanthan gum and acacia gum), and animal-based polymers (such as gelatin and collagen); semi-synthetic polymers, such as cellose-based polymers (such as methyl cellulose, ethyl cellulose, hydroxyethyl cellulose and sodium carboxymethylcellulose), and starch-based polymers (such as soluble starch, carboxymethyl starch and dialdehyde starch); and synthetic polymers, such as vinyl-based polymers (such as polyvinyl alcohol, polyvinylpyrrolidone and polyvinylmethacrylate), acryl-based polymers (such as polyacrylic acid and sodium polyacrylate), polyoxyethylene oxides, and methylvinylether/maleic anhydride copolymers.

Of these, sodium polyacrylate is particularly preferred because of its high gel strength and good water retention. Sodium polyacrylate preferably has an average degree of polymerization of 20,000 to 70,000. Sodium polyacrylate having an average degree of polymerization of less than 20,000 exhibits less thickening effect, failing to provide sufficient gel strength. Conversely, sodium polyacrylate exhibits too high a thickening effect and leads to decreased workability when it has an average degree of polymerization of higher than 70,000. An elastic gel having even higher gel strength can be obtained by using sodium polyacrylate in combination with two or more of the above-described water-soluble polymers since sodium polyacrylate, a highly ionic polymer, forms a polymer complex with the water-soluble polymers.

A humectant may be used in the drug-containing matrix as a constituent. Examples of the humectant include polyols, such as glycerol, propylene glycol and sorbitol. In addition, filler, such as kaolin, zinc oxide, talc, titanium, bentonite, aluminum silicate, titanium oxide, zinc oxide, aluminum metasilicate, calcium sulfate and calcium phosphate, may be added. A solubilizing agent or an absorption enhancer, such as propylene carbonate, crotamiton, 1-menthol, mint oil, limonene and diisopropyl adipate, may also be added. A drug-activity enhancer, such as methyl salicylate, glycol salicylate, 1-menthol, thymol, mint oil, nonanoic acid vanillylamide and capsicum extract, may also be added. When necessary, other ingredients, such as a stabilizer, an antioxidant and an emulsifier, may also be added.

When necessary, the drug-containing matrix may also contain a crosslinking agent or a polymerization agent to further strengthen the drug-containing matrix as well as to impart the water retention property to the drug-containing matrix. The crosslinking agent is properly selected depending on the type of the thickener or other components. For example, when the thickener is polyacrylic acid or a polyacrylate, the crosslinking agent is preferably compounds having at least two epoxy groups in their molecules or a polyvalent metal compound including inorganic acid salts, such as hydrochlorides, sulfates, phosphates and carbonates of Ca, Mg and Al; organic acid salts, such as citrates, tartrates, gluconates and stearates; oxides, such as zinc oxide and silicic anhydride; and hydroxides, such as aluminum hydroxide and magnesium hydroxide.

When the thickener is polyvinyl alcohol, the crosslinking agent or the polymerization agent is preferably adipic acid, thioglycol acid, epoxy compounds (epichlorohydrin), aldehydes, N-methylol compounds, and complex compounds of metallic compound, such as Al, Ti, Zr, Sn, V, Cu, B and Cr.

When the thickener is polyvinylpyrrolidone, the crosslinking agent or the polymerization agent is preferably a methylvinylether/maleic anhydride copolymer, or a polyacid compound or an alkali metal salt thereof (such as polyacrylic acid, tannic acid and derivatives thereof).

When the thickener is polyethylene oxide, the crosslinking agent or the polymerization agent is preferably a peroxide or polysulfone azide. When the thickener is methylvinylether/maleic anhydride copolymer, the crosslinking agent or the polymerization agent is preferably a polyfunctional hydroxyl compound, polyamine, iodine, gelatin, polyvinylpyrrolidone, iron, mercury or lead salt.

When the thickener is gelatin, the crosslinking agent or the polymerization agent is preferably an aldehyde, such as formaldehyde, glutaraldehyde and dialdehyde starch, a diepoxide, such as gluoxal and butadieneoxide, a diketone, such as divinyl ketone, or a diisocyanate. When the thickener is sodium polyacrylate, the crosslinking agent added is preferably a polyvalent metal salt, such as lithium hydroxide, zinc hydroxide, aluminum hydroxide and sodium borate. Zinc salts and aluminum salts promote crosslinking reactions and are thus particularly preferred.

The polyvalent metal salt used as the crosslinking agent is preferably used at a concentration of 0.5 to 1.5 equivalents relative to 1 equivalent of the thickener (or water-soluble polymer). When used at a concentration of less than 0.5 equivalents, the polyvalent metal salt does not sufficiently promote the crosslinking reaction, resulting in low gel strength. When used at a concentration of higher than 1.5 equivalents, the polyvalent metal salt excessively accelerates the crosslinking reaction, resulting in non-uniform gelation and, thus, decreased workability.

An external medicated patch is required to stick firmly to the skin, enhance absorption of the active ingredient by the skin, and contain as much water as possible. The moisture present in the drug-containing matrix removes heat from the skin as it evaporates. The heat absorption causes coolness. The water molecules evaporating from inside the matrix hydrate the stratum corneum and thereby promote the drug absorption. Requirements for the drug-containing matrix include the following: it should not soften near room temperature; it should not cause pain or remain on the skin when the medicated patch is peeled; and it should not cause stickiness.

To meet the above-described requirements, the drug-containing matrix contains 5 to 20 wt %, preferably 10 to 15 wt % of the thickener, 5 to 40 wt % of the humectant, 20 wt % or less of the filler, 10 to 80 wt % of water, 0 to 8 wt % of the solubilizing agent, and 5 wt % or less, preferably 0.5 to 5 wt % of the drug.

The drug used as an active ingredient in the external medicated patch of the present invention can be selected from a variety of drugs to suit the intended application. Examples of analgesic and antiinflammatory agents that can be used in the medicated patch include indomethacin, ketoprofen, flurbiprofen, ibuprofen, felbinac, Ethylene glycol salicylate, methyl salicylate, glycyrrhizinic acid, dipotassium glycyrrhizinate and β-glycyrrhizinic acid.

Blood circulation-promoting agents that can be used in the external medicated patch include tocopherol acetate, capsicum extract, capsaicin, nonanoic acid vanillylamide, benzyl nicotinate and benzyl alcohol. Antiallergic agents that can be used in the external medicated patch include diphenhydramine hydrochloride and chlorpheniramine maleate. Locally stimulating agents that can be used in the external medicated patch include 1-menthol, camphor, mint oil and eucalyptus oil. Local anesthetic agents that can be used in the external medicated patch include lidocaine, benzocaine, dibucaine and tetracaine.

The drugs, for use in the external medicated patch, are not limited to those described above and may be used in combination of two or more as desired.

The amount of the drug used in the drug-containing matrix is properly determined depending on the type and the intended application of the medicated patch (such as poultice-type patch) so that the drug is delivered to the application site at a predetermined effective dose when the medicated patch is applied to the patients.

In the external medicated patch of the present invention, the projection or slack portion of the liner, i.e., the area unattached to the drug-containing matrix, serves as a tab to be held by the user upon peeling of the liner. While the tab may have any suitable width, it is preferably about 5 mm to 20 mm wide and preferably about 10 mm to 15 mm wide.

The liner with the tab that is less than 5 mm wide cannot be held properly. The liner with the tab that has a width of 15 mm or more can be held easily but is less cost-effective because of its increased area and the increased size of the film pouch to contain the medicated patch.

EXAMPLES

Several embodiments to serve as concrete examples of the external medicated patch of the present invention will now be described with reference to the accompanying drawings.

Embodiment 1

Shown in FIG. 1 is an external medicated patch of Embodiment 1 provided as one example of the present invention. The medicated patch is shown in a perspective view in FIG. 1.1, in a side view along the length in FIG. 1.2 and in a side view along the width in FIG. 1.3.

The external medicated patch 1 shown in FIG. 1 is essentially constructed as a laminate including a backing 2, a drug-containing matrix 3 spread over the substantially entire surface of the backing 2, and a liner 4 attached to the surface of the drug-containing matrix 3. The liner 4 is larger in size than the surface of the drug-containing matrix 3 to which the liner is attached. The liner thus includes an area 5 that is unattached to the surface of the drug-containing matrix and extends from each of the four sides of the medicated patch 1.

Specifically, the backing 2 is formed of a stretchable nonwoven fabric. The drug-containing matrix 3 is formed of a base, such as sodium polyacrylate, containing, along with moisture, a drug such as felbinac, an antiinflammatory/analgesic agent. The base is spread over the substantially entire surface of the backing to form the drug-containing matrix. In the medicated patch 1, the liner 4 attached to the surface of the drug-containing matrix 3 is 30 μm thick and formed of a material such as cast polypropylene. The liner 4 is embossed with a diamond pattern. The medicated patch 1 includes the unattached area 5 of the liner 4 that extends from each of the four sides of the medicated patch 1 by about 10 mm.

How to use the medicated patch of Embodiment 1 having the above-described construction and provided as one example of the present invention will now be described.

In order to apply the external medicated patch to a desired application site, the liner needs to be peeled first to expose the surface of the drug-containing matrix covered by the liner. To do this, the user holds the unattached area 5 of the liner 4 which projects from the surface of the drug-containing matrix with the fingers of one hand and peels the stepped portion at the end of the medicated patch with the fingers of the other hand. In this fashion, the drug-containing matrix can be readily exposed. Once the liner 4 has been peeled completely, the user applies the exposed surface of the drug-containing matrix to the application site.

Having the essential construction as described above, the medicated patch of Embodiment 1 of the present invention has unique characteristics as described below.

Specifically, the step resulting from the difference in area between the liner 4 and the drug-containing matrix 3, i.e., the area 5 of the liner unattached to the surface of the drug-containing matrix, provides a starting point for the peeling of the liner 4. This construction allows the user to readily peel the liner 4 from any side without rubbing the edge of the medicated patch 1 with fingers.

Thus, the liner does not require particular dexterity for its removal and can therefore be unconsciously peeled even by aged people. Should the user fail to peel the liner in a proper manner, the user can still peel it without any difficulty using the conventional method in which the user rubs the edge of the backing with the fingers.

Embodiment 2

Shown in FIG. 2 is an external medicated patch of Embodiment 2 provided as another example of the present invention. The medicated patch is shown in a perspective view in FIG. 2.1, in a side view along the length in FIG. 2.2 and in a side view along the width in FIG. 2.3.

Reference numerals in FIG. 2 denote the same elements as in FIG. 1.

Unlike the liner used in the external medicated patch of the previous Embodiment 1, the liner 4 used in the external medicated patch 1 of Embodiment 2 and attached to the surface of the drug-containing matrix 3 has an unattached area 5 extending from each of the two short sides at the longitudinal ends of the medicated patch 1.

Specifically, the backing 2 is formed of a stretchable nonwoven fabric. The drug-containing matrix 3 is formed of a base ingredient, such as sodium polyacrylate, containing, along with water, a drug such as indomethacin. The base ingredient is spread over the substantially entire surface of the backing 2 to form the drug-containing matrix 3. The liner 4 is a 38 μm-thick transparent polyethylene terephthalate film. The medicated patch includes the unattached areas 5 of the liner 4 that each extend from each of the two short sides of the medicated patch 1 by 10 mm.

Having the above-described construction, the external medicated patch 1 of Embodiment 2 can be used in the substantially same manner as the external medicated patch of Embodiment 1. One difference is that the liner 4, unlike the liner used in the medicated patch of Embodiment 1, lacks the unattached areas that extend from both the long sides in the longitudinal direction of the medicated patch at the ends as viewed along the width of the medicated patch and thus has a correspondingly decreased area. As a result, the liner 4 of Embodiment 2 is more cost-effective than the liner of Embodiment 1.

Embodiment 3

Shown in FIG. 3 is an external medicated patch of Embodiment 3 provided as yet another example of the present invention. The medicated patch is shown in a perspective view in FIG. 3.1 and in a side view along the length in FIG. 3.2.

Reference numerals in FIG. 3 denote the same elements as in FIG. 1.

The external medicated patch 1 of Embodiment 3 is essentially constructed as a laminate including a backing 2, a drug-containing matrix 3 spread over the substantially entire surface of the backing 2, and a liner 4 attached to the surface of the drug-containing matrix 3. The liner 4 is larger in size than the surface of the drug-containing matrix 3 to which the liner is attached. The liner 4 includes a slack portion 6 that is unattached to the drug-containing matrix and projects upward from the surface of the drug-containing matrix.

Specifically, the backing 2 used in the external medicated patch 1 of Embodiment 3 of the present invention is formed of a stretchable woven fabric. The drug-containing matrix 3 is formed of a base, such as sodium polyacrylate, containing, along with water, a drug such as methyl salicylate. The base is spread over the substantially entire surface of the backing 2 to form the drug-containing matrix 3. The liner 4 attached to the surface of the drug-containing matrix 3 is a 30 μm-thick cast polypropylene film embossed to give it a silk cloth texture. The unattached area or the slack portion 6 of the liner 4 is sized about 10 mm and projects at a position about two-thirds from one end of the medicated patch. The liner 4 does not extend from any of the four sides of the drug-containing matrix 3.

To apply the external medicated patch 1 of Embodiment 3 having the above-described construction, the user first holds with the fingers of one hand the slack portion 6 provided at a position about two-thirds from one end of the medicated patch while gently holding the end of the medicated patch with the fingers of the other hand. The user then pulls the slack portion 6 to lift and peel the liner 4 from the end of the medicated patch. Finally, the user applies the exposed surface of the drug-containing matrix to the application site. The medicated patch can be applied easily in this fashion.

In this case, the liner 4 includes the unattached area or slack portion 6 and therefore has a larger area than the surface of the drug-containing matrix. However, the liner 4 does not include any unattached areas that extend from the long sides or short sides of the medicated patch. Thus, the finished product of the medicated patch has the same size as the conventional medicated patch and can be packaged in a pouch having the same size as the conventional product. For this reason, the medicated patch of Embodiment 3 is even more cost-effective than the medicated patch of Embodiment 2.

INDUSTRIAL APPLICABILITY

As set forth, the present invention provides an external medicated patch that includes a backing, a hydrated adhesive drug-containing matrix that is spread substantially entirely over one surface of the backing, and a liner that is larger in size than the surface of the drug-containing matrix to which the liner is attached. The step resulting from the difference in area between the liner and the drug-containing matrix provides a starting point for the peeling of the liner. This construction allows the user to readily peel the liner without rubbing the edge of the medicated patch with the fingers. Thus, the liner can be readily peeled even by aged people and is therefore of significant medical importance.

BRIEF DESCRIPTION OF THE DRAWINGS

FIG. 1.1 is a perspective view of a medicated patch according to Embodiment 1 of the present invention.

FIG. 1.2 is a side view along the length of the medicated patch of Embodiment 1.

FIG. 1.3 is a side view along the width of the medicated patch of Embodiment 1.

FIG. 2.1 is a perspective view of a medicated patch according to Embodiment 2 of the present invention.

FIG. 2.2 is a side view along the length of the medicated patch of Embodiment 2.

FIG. 2.3 is a side view along the width of the medicated patch of Embodiment 2.

FIG. 3.1 is a perspective view of a medicated patch according to Embodiment 3 of the present invention.

FIG. 3.2 is a side view along the length of the medicated patch of Embodiment 3.

FIG. 4.1 is a perspective view of a conventional medicated patch.

FIG. 4.2 is a side view along the length of the conventional medicated patch.

FIG. 5.1 is a perspective view of another conventional medicated patch.

FIG. 5.2 is a side view along the length of the conventional medicated patch.

DESCRIPTION OF THE REFERENCE NUMERALS

Figure 6:
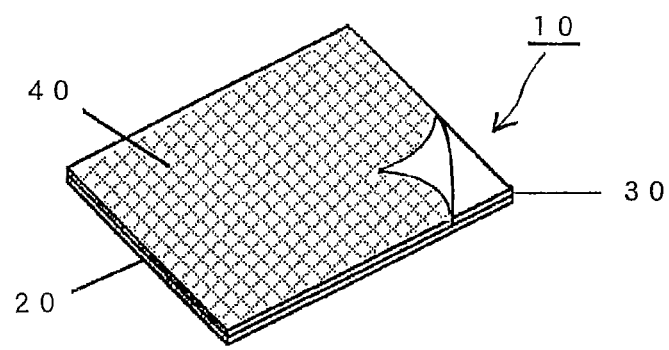
FIG. 6 is a diagram illustrating the manner in which the liner of the conventional medicated patch is peeled.

1 external medicated patch
2 backing
3 drug-containing matrix
4 peelable film (liner)
5 unattached area
6 slack portion
10 external medicated patch
20 backing
30 drug-containing matrix
40 peelable film (liner)
50 tear line

The invention claimed is:
1. An external medicated patch comprising: a backing unattached on one surface; an aqueous adhesive drug-containing matrix that is spread substantially entirely over one surface of the backing opposite the unattached surface of the backing, and an attached single-sheet liner that is larger in size than a surface of the drug-containing matrix to which the attached single-sheet liner is attached, wherein the attached single-sheet liner prior to peeling fully covers the surface of the drug-containing matrix and includes an unattached slack portion that projects upward from the surface of the drug-containing matrix, wherein the drug-containing matrix comprises a water content between about 30% to about 80%.

* * * * *